(12) United States Patent
Cook

(10) Patent No.: US 7,934,502 B2
(45) Date of Patent: May 3, 2011

(54) SELF-PRESSURIZING SUPRAGLOTTIC AIRWAY

(75) Inventor: Daniel J Cook, St. Louis, MO (US)

(73) Assignee: Cookgas, LLC, St. Louis, MO (US)

( * ) Notice: Subject to any disclaimer, the term of this patent is extended or adjusted under 35 U.S.C. 154(b) by 995 days.

(21) Appl. No.: 11/747,486

(22) Filed: May 11, 2007

(65) Prior Publication Data

US 2008/0276936 A1    Nov. 13, 2008

(51) Int. Cl.
*A61M 16/00* (2006.01)
*A62B 9/06* (2006.01)

(52) U.S. Cl. .......... 128/207.15; 128/207.14; 128/200.26

(58) Field of Classification Search ............. 128/200.26, 128/206.26, 207.14, 207.15, 207.16
See application file for complete search history.

(56) References Cited

U.S. PATENT DOCUMENTS

| | | | |
|---|---|---|---|
| 678,814 A | 7/1901 | Riggs |
| 1,345,425 A | 7/1920 | Wells |
| 2,335,741 A | 11/1943 | Contaldi |
| 2,787,010 A | 4/1957 | Uphoff |
| 3,139,088 A | 6/1964 | Galleher, Jr. |
| 3,434,100 A | 3/1969 | Dykzeul |
| 3,606,669 A | 9/1971 | Kemble |
| 3,734,100 A | 5/1973 | Walker et al. |
| 3,756,601 A | 9/1973 | Frey et al. |
| 3,945,069 A | 3/1976 | Cecil |
| 4,146,034 A | 3/1979 | Gupta |
| 4,231,365 A | 11/1980 | Scarberry |
| 4,327,720 A | 5/1982 | Bronson et al. |
| 4,340,046 A | 7/1982 | Cox |
| 4,388,076 A | 6/1983 | Waters |
| 4,444,201 A | 4/1984 | Itoh |
| 4,509,512 A | 4/1985 | LeClercq |
| 4,509,514 A | 4/1985 | Brain |
| 4,520,810 A | 6/1985 | Weiss |
| RE31,948 E | 7/1985 | Deutsch et al. |
| 4,540,959 A | 9/1985 | Saad |
| 4,582,056 A | 4/1986 | McCorkle, Jr. |
| 4,593,687 A | 6/1986 | Gray |
| 4,661,028 A | 4/1987 | Sanger |
| 4,674,496 A | 6/1987 | Svadjian et al. |
| 4,751,922 A | 6/1988 | DiPietropolo |
| 4,791,923 A | 12/1988 | Shapiro |
| 4,825,861 A | 5/1989 | Koss |
| 4,863,439 A | 9/1989 | Sanderson |
| 4,872,483 A | 10/1989 | Shah |
| 4,895,533 A | 1/1990 | Yagi |
| 4,919,127 A | 4/1990 | Pell |
| 4,995,388 A | 2/1991 | Brain |
| 5,024,220 A | 6/1991 | Holmgreen et al. |

(Continued)

OTHER PUBLICATIONS

"Products—LMA Fastrach," http://www.lmana.com/prod/components/products/lma_fastrach.html, printed on Jun. 19, 2005, one page.

(Continued)

*Primary Examiner* — Justine R Yu
*Assistant Examiner* — Valerie Skorupa
(74) *Attorney, Agent, or Firm* — Lewis, Rice & Fingersh, L.C.

(57) ABSTRACT

A supraglottic airway of the type used to facilitate lung ventilation and the insertion of endo-tracheal tubes or related medical instruments through a patient's laryngeal opening where the shield is designed to have an internal increase in pressure during assisted inhalation such as positive-pressure ventilation.

20 Claims, 8 Drawing Sheets

U.S. PATENT DOCUMENTS

| | | |
|---|---|---|
| 5,033,919 A | 7/1991 | Choe |
| 5,037,251 A | 8/1991 | Roth |
| 5,042,475 A | 8/1991 | LaBombard |
| 5,071,413 A | 12/1991 | Utterberg |
| 5,197,463 A | 3/1993 | Jeshuran |
| 5,218,970 A | 6/1993 | Turnbull et al. |
| 5,222,487 A | 6/1993 | Carr et al. |
| 5,253,658 A | 10/1993 | King |
| 5,277,178 A | 1/1994 | Dingley |
| 5,279,610 A | 1/1994 | Park et al. |
| 5,282,464 A | 2/1994 | Brain |
| 5,303,697 A | 4/1994 | Brain |
| 5,324,080 A | 6/1994 | McNaughton et al. |
| 5,326,196 A | 7/1994 | Noll |
| 5,340,165 A | 8/1994 | Sheppard |
| 5,355,879 A | 10/1994 | Brain |
| 5,391,248 A | 2/1995 | Brain |
| 5,392,774 A | 2/1995 | Sato |
| 5,393,101 A | 2/1995 | Matkovich |
| 5,477,852 A | 12/1995 | Landis et al. |
| 5,509,408 A | 4/1996 | Kurtis |
| 5,513,627 A | 5/1996 | Flam |
| 5,527,316 A | 6/1996 | Stone |
| 5,529,582 A | 6/1996 | Fukuhara |
| 5,545,048 A | 8/1996 | Maeda |
| 5,546,937 A | 8/1996 | Stuart et al. |
| 5,562,371 A | 10/1996 | Reed |
| 5,562,673 A | 10/1996 | Koblish et al. |
| 5,569,222 A | 10/1996 | Haselhorst et al. |
| 5,579,762 A | 12/1996 | Lee |
| 5,584,290 A | 12/1996 | Brain |
| 5,588,424 A | 12/1996 | Insler et al. |
| 5,590,643 A | 1/1997 | Flam |
| 5,623,921 A | 4/1997 | Kinsinger et al. |
| 5,632,271 A | 5/1997 | Brain |
| 5,643,174 A | 7/1997 | Yamamoto et al. |
| 5,653,231 A | 8/1997 | Bell |
| 5,655,519 A | 8/1997 | Alfery |
| 5,682,880 A | 11/1997 | Brain |
| 5,711,296 A | 1/1998 | Kolobow |
| 5,713,348 A | 2/1998 | Pell |
| 5,720,749 A | 2/1998 | Rupp |
| 5,743,258 A * | 4/1998 | Sato et al. ............ 128/207.15 |
| 5,772,643 A | 6/1998 | Howell et al. |
| 5,787,879 A | 8/1998 | Gibson |
| 5,878,745 A | 3/1999 | Brain |
| 5,881,726 A | 3/1999 | Neame |
| 5,896,858 A | 4/1999 | Brain |
| 5,937,860 A | 8/1999 | Cook |
| 5,947,120 A | 9/1999 | Bailey |
| 5,961,489 A | 10/1999 | Hirota |
| 5,979,445 A | 11/1999 | Neame et al. |
| 6,021,779 A | 2/2000 | Pagan |
| 6,196,224 B1 | 3/2001 | Alfery |
| 6,240,922 B1 | 6/2001 | Pagan |
| 6,261,401 B1 | 7/2001 | Pagan |
| 6,374,827 B1 | 4/2002 | Bowden et al. |
| 6,386,199 B1 | 5/2002 | Alfery |
| 6,422,239 B1 | 7/2002 | Cook |
| 6,450,164 B1 | 9/2002 | Banner et al. |
| 6,612,305 B2 | 9/2003 | Fauza |
| 6,631,720 B1 | 10/2003 | Brain |
| 6,668,821 B2 | 12/2003 | Christopher |
| 6,705,318 B1 | 3/2004 | Brain |
| 6,705,320 B1 | 3/2004 | Anderson |
| 6,705,321 B2 | 3/2004 | Cook |
| 6,705,322 B2 | 3/2004 | Chang |
| 6,729,325 B2 | 5/2004 | Alfery |
| 6,892,731 B2 | 5/2005 | Cook |
| 6,899,147 B2 | 5/2005 | Ogawa et al. |
| 6,923,176 B2 | 8/2005 | Ranzinger |
| 6,935,153 B2 | 8/2005 | Frigo et al. |
| 6,983,744 B2 | 1/2006 | Alfery |
| 7,013,899 B2 | 3/2006 | Alfery |
| 7,021,686 B2 | 4/2006 | Glasgow et al. |
| 7,040,312 B2 | 5/2006 | Alfery et al. |
| 7,040,322 B2 | 5/2006 | Fortuna |
| 7,096,868 B2 | 8/2006 | Tateo et al. |
| 7,097,802 B2 | 8/2006 | Brain |
| 7,128,071 B2 | 10/2006 | Brain |
| 2001/0050082 A1 | 12/2001 | Christopher |
| 2003/0051734 A1 * | 3/2003 | Brain ............ 128/207.15 |
| 2004/0020491 A1 | 2/2004 | Fortuna |
| 2004/0079364 A1 | 4/2004 | Christopher |
| 2005/0016529 A1 | 1/2005 | Cook |
| 2005/0051173 A1 | 3/2005 | Brain |
| 2005/0139220 A1 | 6/2005 | Christopher |
| 2006/0027238 A1 * | 2/2006 | Lin ............ 128/207.15 |
| 2006/0076021 A1 | 4/2006 | Chang |
| 2006/0180156 A1 | 8/2006 | Baska |
| 2006/0207597 A1 | 9/2006 | Wright |
| 2007/0028923 A1 | 2/2007 | Souris et al. |
| 2007/0102001 A1 | 5/2007 | Brain |
| 2007/0137651 A1 | 6/2007 | Glassenberg et al. |
| 2007/0246050 A1 | 10/2007 | Parikh et al. |
| 2008/0078398 A1 | 4/2008 | Cook |

OTHER PUBLICATIONS

"9c Removal of LMA-Fastrach Prior to Extubation," LMA-Fastrach Instructional Manual, www.lmana.com/docs/fastrach_instruction.pdf, Feb. 2002, pages cover (2 pages), 26-27.

Byrd, Jr., R.P."Ventilation, Mechanical," http://www.emedicine.com/med/topic3370.htm, Jul. 6, 2006, pp. 1-13.

"Ambu Product Information," Ambu A/S, 2007, pp. 1-18, Denmark.

"Intersurgical Complete Respiratory Systems," http://www.intersurgical.com/productscatalog/choosegroup.aspx?cm..., printed on Apr. 11, 2007, one page.

"LMA Airway Instruction Manual," The Laryngeal Mask Company Limited, www.lmana.com/docs/LMA_Airways_Manual.pdf, 2005, pp. 1-23.

International Search Report, International Patent Application No. PCT/US2008/060425, mailed Sep. 29, 2008, 11 pages.

* cited by examiner

SELF-PRESSURIZING SUPRAGLOTTIC AIRWAY

BACKGROUND

1. Field of the Invention

The invention relates to an artificial airway device, more specifically to a supraglottic airway designed to have increased internal pressure during introduction of artificial positive-pressure ventilation.

2. Description of the Related Art

In general, supraglottic airways such as laryngeal masks allowing for both rapid lung ventilation and the insertion of medical instruments and tubes into the laryngeal openings of patients have been described in patents, such as U.S. Pat. No. 4,509,514 to Brain and U.S. Pat. Nos. 6,422,239 and 5,937,860 to Cook the entire disclosures of which were herein incorporated by reference. Laryngeal masks generally consist of two major components, a breathing tube and an inflatable or rigid shield, these devices are inserted into a patient's throat, and when properly positioned, cover the laryngeal opening. A seal is then formed around the circumference of the laryngeal opening by the inflation of a ring-like structure located toward the front of the mask (patient end). Inflation of the ring exerts pressure against the front, sides, and rear portions of the oropharynx, securing the device in place such that the laryngeal opening is positioned in alignment with a recessed cavity in the mask face. Alternatively, the structure of the shield may be formed as a large semi-rigid plastic construct which generally serves to seal by contouring to the shape of the throat and imparting pressure on the throat by its own size and shape effectively filing available space.

Extending from a point external to the oral cavity, the flexible breathing tube terminates within the recessed cavity, aligned axially with the laryngeal opening. The positioning of the flexible breathing tube allows the passage of endo-tracheal tubes or related medical instruments into the laryngeal opening, in addition to allowing for positive-pressure lung ventilation.

While current supraglottic airways such as laryngeal masks can provide for improved placement and breathing over a traditional endotracheal tube, they can be improved. In particular, the use of inflated structures or semi-rigid plastic constructs to hold the device in place in the throat can lead to undesirable pressure on throat tissue. Current designs seal the laryngeal opening inside the recess by exerting a constant pressure on surrounding tissue effectively forcing the structure of the mask into the walls of the throat while it is in place. This constant pressure is generally not relieved until the device is removed. While the structure of these devices are generally made pliable and soft so as to minimize potential damage from their near constant contact with throat tissues, the constant pressure they impart on potentially sensitive structures in the throat can, in some cases, lead to tissue fatigue and damage.

The problem is exacerbated by the fact that the person inserting the airway generally has little to no control on the pressure exerted by the airway and often has no indication thereof. Thus, the device can easily be accidentally over-inflated or over-sized exerting more pressure than is necessary or desirable on the tissue of the throat, often without realizing it.

SUMMARY

The following is a summary of the invention in order to provide a basic understanding of some aspects of the invention. This summary is not intended to identify key or critical elements of the invention or to delineate the scope of the invention. The sole purpose of this section is to present some concepts of the invention in a simplified form as a prelude to the more detailed description that is presented later.

Because of these and other problems in the art, described herein is a supraglottic airway primarily intended to facilitate lung ventilation and the insertion of endo-tracheal tubes or related medical instruments into a patient's trachea as needed during general anesthesia, intensive care, critical patient care, or at any other time that ventilation would be desired. In an embodiment of such a supraglottic airway, the airway comprises a flexible ventilation tube and a positioning shield which is characterized as being "self-pressurizing." This term refers to the fact that the shield generally imparts an increased sealing pressure on the throat when under positive pressure from assisted ventilation than it does during spontaneous exhalation. In this way the shield is generally only "pressurized" intermittently and only exerts its highest sealing pressure on throat tissues in a limited fashion. The shield generally conforms to the anatomy of the oropharynx region surrounding the laryngeal opening, and is securely affixed to the distal end of the ventilation tube.

Described herein, among other things is a supraglottic airway comprising; a respiratory tube having a distal end, a proximal end, and a length therebetween, the respiratory tube having a hollow interior; and a shield comprising a posterior base and a sealing ring surrounding the posterior base and defining an inner volume within the sealing ring and a cavity above the posterior base; wherein the shield is attached to the distal end of the respiratory tube so that the hollow interior of the respiratory tube is in fluid communication with the cavity; wherein the hollow interior and the cavity jointly define an air path; and wherein the inner volume of the sealing ring is capable of fluid communication with the air path.

In an embodiment of the airway the respiratory tube is smoothly curved and may comprise a connector removeably attached to the proximal end of the respiratory tube.

The airway may be constructed using any technique of manufacture such as, but not limited to, blow-molding or injection molding. The airway may be intended to be disposable, that is for single use, or may be intended for sterilization and reuse between patients.

In an embodiment of the airway the air path may be in fluid communication with the inner volume via a port. This port may be located in the respiratory tube in a side of the sealing ring opening into the cavity and may comprise a single hole, multiple holes, or an elongated, potentially continuous, slit which may circumscribe the cavity.

There is also described herein a supraglottic airway comprising; a respiratory tube having a distal end, a proximal end, and a length therebetween, the respiratory tube defining an air path therethrough; and a shield comprising a posterior base and a sealing ring surrounding the posterior base and defining an inner volume within the sealing ring and a cavity above the posterior base, wherein the shield is attached to the distal end of the respiratory tube so that the air path in the respiratory tube is in fluid communication with the cavity and wherein the cavity is in fluid communication with an inner volume of the sealing ring.

There is also described herein, a supraglottic airway comprising; a respiratory tube having a distal end, a proximal end, and a length therebetween, the respiratory tube defining an air path therethrough; and a shield comprising a posterior base and a sealing ring surrounding the posterior base and defining an inner volume within the sealing ring, wherein the shield is attached to the distal end of the respiratory tube so that the air path in the respiratory tube is in fluid communication with the inner volume of the sealing ring.

There is also described herein a method of providing an artificial airway to a human comprising: placing in the throat of a human, a supraglottic airway comprising; a respiratory tube having a distal end, a proximal end, and a length therebetween, the respiratory tube defining a hollow interior; and a shield comprising a posterior base and a sealing ring surrounding the posterior base and defining an inner volume within the sealing ring and a cavity above the posterior base, wherein the shield is attached to the distal end of the respiratory tube and the cavity and the hollow interior jointly define an air path; attaching the proximal end to a ventilation apparatus; and forcing air into the air path to provide air to the patient; wherein, the act of forcing air into the air path alters the pressure in the inner volume of the sealing ring.

Depending on the embodiment of the method the alteration of pressure in the inner volume of the sealing ring may alter the size of the sealing ring as air is forced into the air path, increase the strength of seal of the sealing ring to the throat or increase the pressure the sealing ring imparts on the throat.

There is still further described herein, an artificial breathing system comprising: a supraglottic airway including; a respiratory tube having a distal end, a proximal end, and a length therebetween, the respiratory tube defining a hollow interior therethrough; and a shield comprising a posterior base and a sealing ring surrounding the posterior base and defining an inner volume within the sealing ring and a cavity above the posterior base, wherein the shield is attached to the distal end of the respiratory tube and the cavity and the hollow interior jointly define an air path; and a ventilation apparatus designed to increase pressure in the air path which is attached to the proximal end; wherein, when the ventilation apparatus increases pressure in the air path it also alters the pressure in the inner volume in the sealing ring.

Depending on the embodiment of the system the alteration of pressure in the inner volume of the sealing ring may alter the size of the sealing ring as air is forced into the air path, increase the strength of seal of the sealing ring to the throat or increase the pressure the sealing ring imparts on the throat.

In an embodiment of the system, there is a port interconnecting the inner volume of the sealing ring to at least one of the cavity or the hollow interior, the port allowing the alteration in the pressure of the sealing ring. This port may be located in the respiratory tube in a side of the sealing ring opening into the cavity and may comprise a single hole, multiple holes, or an elongated, potentially continuous, slit which may circumscribe the cavity.

There is still further described herein, a supraglottic airway comprising; a respiratory tube having a distal end, a proximal end, and a length therebetween, the respiratory tube having a hollow interior; a shield comprising a posterior base and a sealing ring surrounding the posterior base and defining a cavity above the posterior base; and means for allowing fluid communication between an inner volume of the sealing ring and at least one of the cavity or the hollow interior of the respiratory tube.

DESCRIPTION OF THE PREFERRED EMBODIMENT(S)

The following detailed description illustrates by way of example and not by way of limitation. Described herein, among other things, is an embodiment of a supraglottic airway which includes a shield for sealing with the larynx which is designed to exert greater pressure, and therefore a stronger seal, when an assisted inhalation is being provided for the patient during positive-pressure ventilation. Specifically, the supraglottic airway has a shield (201) including a sealing ring (401). The ring (401) is in gaseous (or more generally fluid) communication with the airway path through which artificial respiration air is provided to the patient. While the supraglottic airway described herein incorporates certain features in the shape and arrangement of the shield (201) for improved placement in the airway, it should be recognized that these features are not required and the sealing rings (401) and related structures discussed herein can be used on airways of other shapes and forms.

Figure 1:
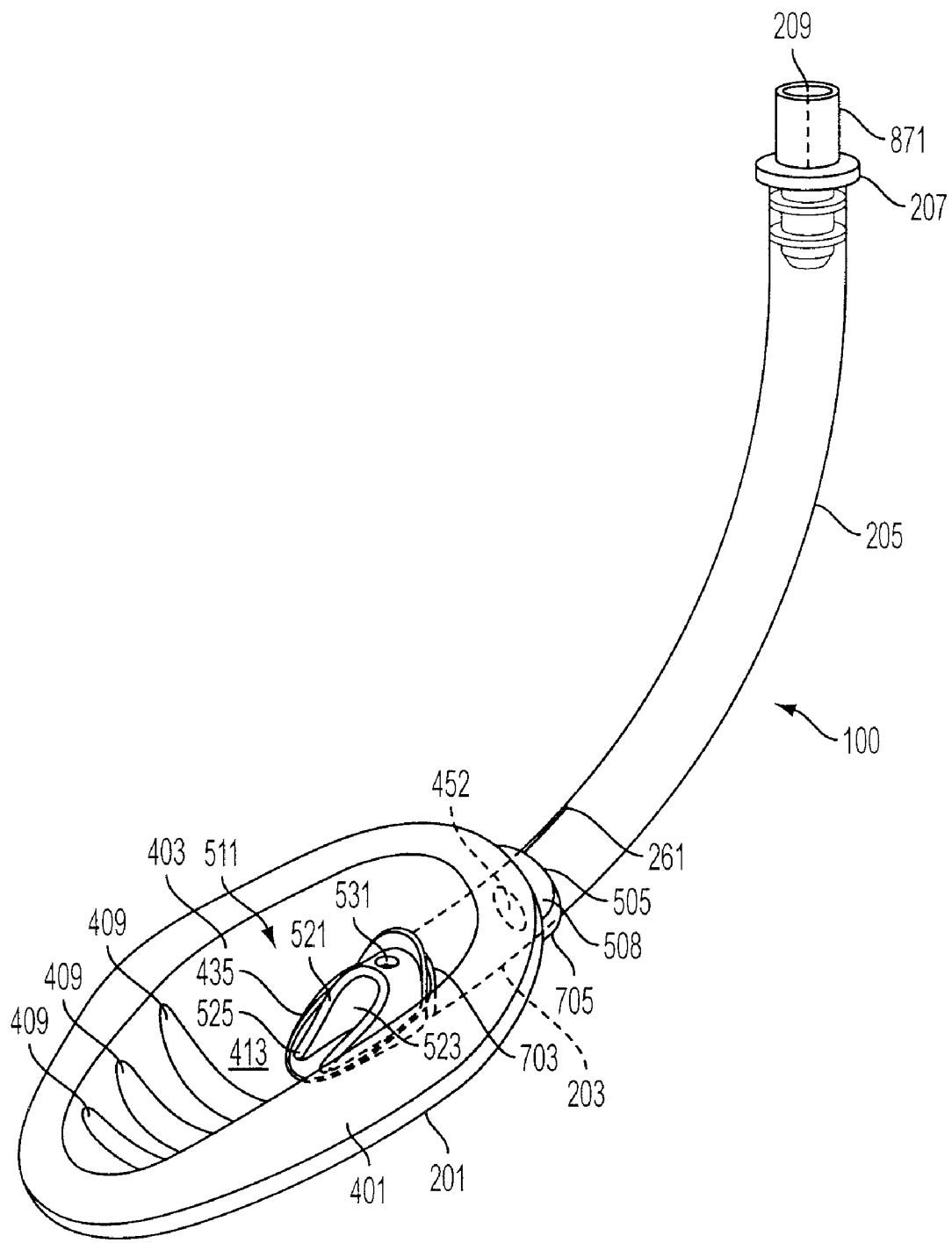
FIG. 1 shows a perspective view of an embodiment of a self-pressurizing laryngeal mask as assembled.

FIG. 1 provides for an embodiment of a supraglottic airway (100) in the form of removable laryngeal mask airway. This mask is chosen as an exemplary form of supraglottic airway (100) including a self-pressurizing sealing ring (401). It is in no way intended to be descriptive of all airways upon which a self-pressurizing sealing ring (401) may be used in other embodiments.

In the depicted embodiment of FIG. 1 the airway (100) generally comprises two major components. There is a respiratory tube (205) generally formed into an arcuate curve and a positioning shield (201) which is secured toward the distal end (203) of the respiratory tube (205). The airway (100) is generally composed of a relatively soft flexible material such as, but not limited to, silicone-rubber polymer or plastics.

Figure 5:
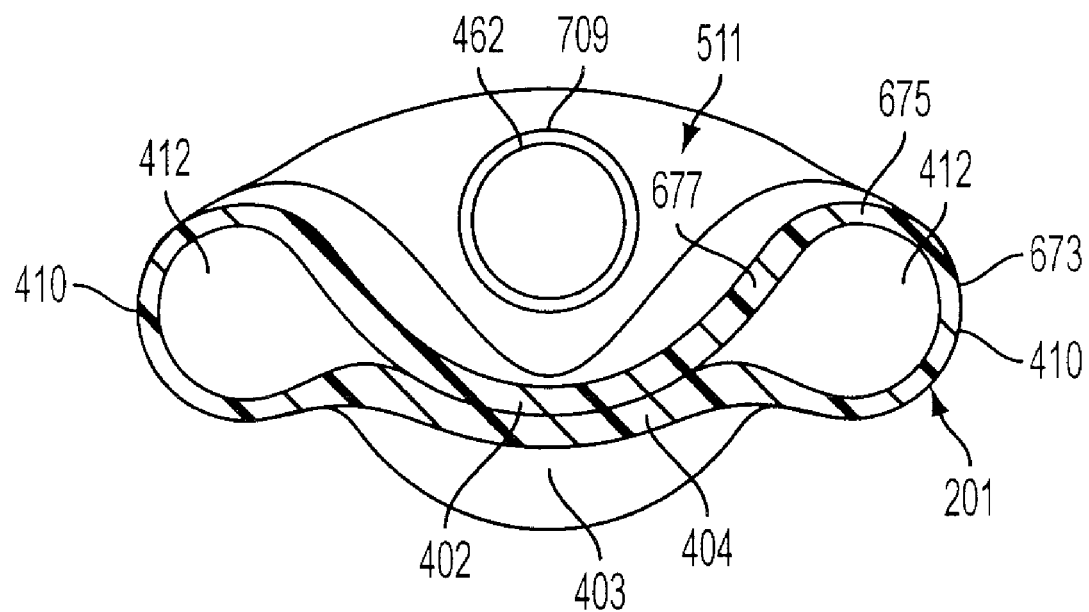
FIG. 5 shows a cut-through along line 5-5 in FIG. 3.

The positioning shield (201) comprises a generally wedge-shaped flexible sealing ring (401) with a pliable molded posterior base (403) attached thereto so that the posterior base (403) forms the base of, and the sealing ring (401) generally surrounds, a cavity (511). The sealing ring (401) is also generally sized and shaped to generally conform to the approximate available space in the oropharynx region without significant distortion or causing significant displacement of throat surfaces. Depending on embodiment, the sealing ring (401) may comprise a number of different structures and may be ellipsoidal, toroidal, or of similar shape. As shown in FIG. 5, the sealing ring (401) also generally includes an inner volume (412), which may be generally sealed, or more open, depending on embodiment.

The posterior base (403) is secured longitudinally within a space in the center of the sealing ring (401) to form cavity (511). The posterior base (403) is generally attached in a fashion to form an elongated and tapered hemisphere relative to the generally major plane of the sealing ring (401) so as to give the shield (201) an overall shape such as that seen in the FIGS. In the depicted embodiment, there are semi-rigid raised ridges (409) positioned longitudinally parallel to each other along the surface (413) of the posterior base (403) "inside" the space of the sealing ring (401). This space above the posterior base (403) and "inside" the sealing ring (401) is defined herein as a cavity (511).

Figure 9:
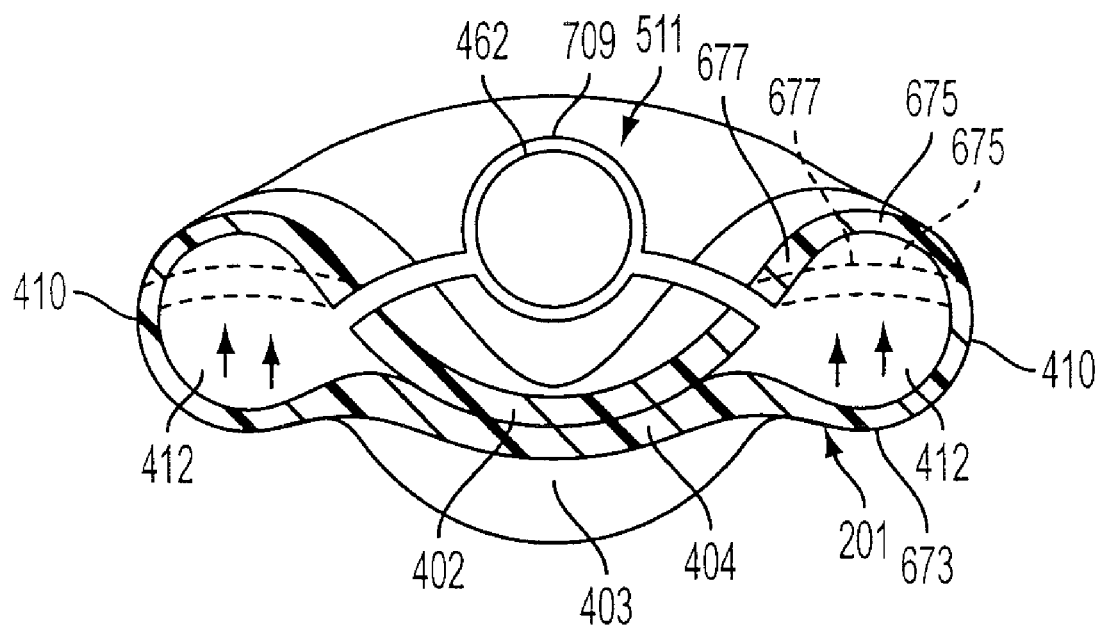
FIG. 9 shows a shape of the shield of FIG. 7 when there is no airflow into the hollow interior of the sealing ring and expansion from such flow.

The sealing ring (401) may comprise a number of different shapes or structures but will generally comprise a section extending upward from the posterior base (403) so as to form the cavity (511) in the shield (201). The sealing ring (401) is generally constructed of a flexible material which is capable of being moved when placed under the influence of air pressure on the order of that expected during positive-pressure ventilation of a patient. This movement will be characterized as expansion, which may comprise inflation such as in a balloon, or may be a shifting or movement of various structures to have a generally larger displacement. An embodiment of the expansion of a sealing ring (401) is shown in FIG. 9 and generally provides the expected type of flexibility when internally exposed to increased pressure.

Figure 6:
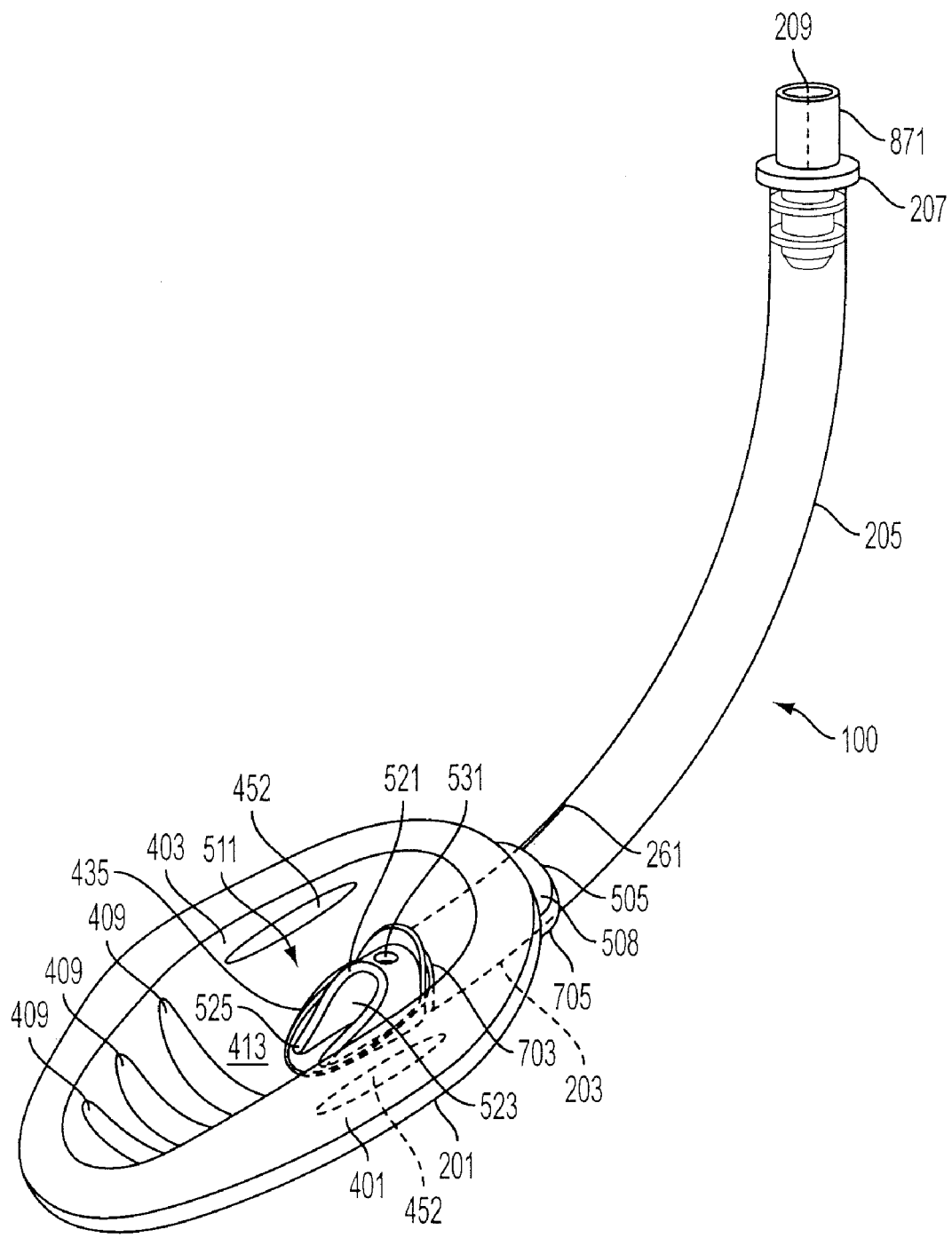
FIG. 6 shows a perspective view of another embodiment of a self-pressurizing laryngeal mask as assembled.
Figure 7:
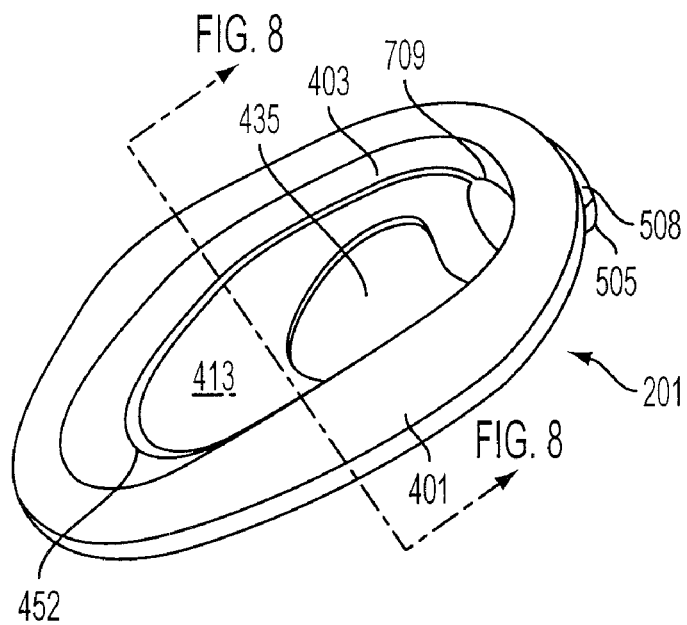
FIG. 7 shows a perspective view of another embodiment of a shield
Figure 8:
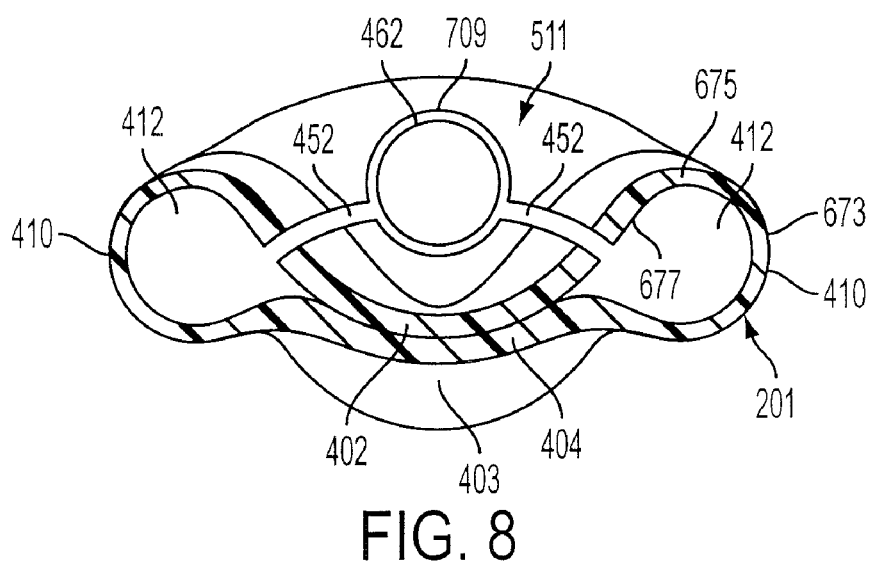
FIG. 8 shows a cut-through along line 8-8 in FIG. 7

In the embodiments of FIGS. 1-6, the sealing ring (401) comprises a ring shape which is itself hollow and encloses a generally hollow inner volume (412) as well as forming the cavity (511). In the embodiment of FIGS. 7-8, the sealing ring (401) comprises a hollow channel which has been formed into a ring shape. Generally, the sealing ring (401) is designated as having an exterior side (673) and an upper surface (675) which bends generally inward toward the center of the posterior base (403) from the exterior side (673). The upper surface (675) may then be connected to an inner side (677) which is directed back down and toward the surface of the posterior base (403). Depending on embodiment, the inner side (677) may attach to the posterior base (403) so as to provide the sealing ring (401) with the tube-like structure discussed in conjunction with FIGS. 1-6 or may not providing a more channel-like structure as discussed in conjunction with FIGS. 7 and 8. FIGS. 1, 5 and 6 provide for perspective and cut-through drawings of shields which are more tubular, while FIGS. 7-8, which show the inner side (677) extending a predetermined distance toward the posterior base (403) before ending, show the inner side (677) being suspended above the posterior base (403).

The shield (201) in the depicted embodiment of FIG. 1, is connected to the respiratory tube (205) by means of a hollow wedge (501) which allows the air pathway defined within the respiratory tube (205) to pass through the shield (201) and into the cavity (511) formed above the posterior base (403) and inside the recess of the sealing ring (401). In a preferred assembly, the hollow wedge (501) is attached generally to the distal end (203) of the respiratory tube (205) as is visible in FIG. 4 and comprises a somewhat more rigid construction than the other components. The wedge section may be inserted into the end of the respiratory tube (205), or may be co-molded with the respiratory tube (205) and/or shield (201) in alternative embodiments. The wedge section may include the wedge (501) as well as a raised disk (553) to be utilized in connection to the shield (201) if those parts are not co-molded. In the event that the airway (100) is molded as a single piece, such disk (553) is clearly unnecessary. In still further embodiments the wedge (501) may be modified in shape from that depicted or may be completely eliminated providing for a connection with an alternative shape to the connection between the respiratory tube (205) and the shield (201) depicted in the FIGS.

In the embodiment of FIG. 1, the respiratory tube (205) passes through a first peripheral seal (703) to exit the cavity (511). This first seal will generally be an airtight seal, but that is by no means required. There is a second peripheral seal (705) towards the proximal end (505) of the inflatable positioning shield (201) which generally provides an airtight seal isolating the air region internal to the cavity (511) and/or internal to the respiratory tube (403) from the air region outside the shield (201) should the cavity (511) and proximal end (207) of the respiratory tube (205) be sealed. This sealing will be discussed later in more detail.

The wedge (501) therefore gives an access into the cavity (511) from the interior of the respiratory tube (205) allowing air to pass from the cavity (511) into the distal end (203) of the respiratory tube (205) and from there out the proximal end (207) of the respiratory tube (205) or vice-versa. The wedge (501) is generally formed into an angle (521) to the length of the respiratory tube (205) which is generally between 0 and 90 degrees and preferably about 30 to about 35 degrees with the posterior base (403), forming an elongated elliptically shaped distal lumen (523) open to the interior of the cavity (511) and interior of the respiratory tube (205), There may also be included a ventilation lumen (531) through the wedge (501) to provide an alternate airway passage in the event the distal lumen (523) becomes obstructed during patient lung ventilation. The ventilation lumen (531) also generally prevents the formation of a pressure differential between the cavity (511) and flexible respiratory tube (205). Absent a pressure differential, any object obstructing the distal lumen (523) will not generally become inextricably lodged.

In order to provide that air introduced into the airway (100) for use by the patient be able to pressurize the sealing ring (401), there is provided a fluid communication port (452) which allows for fluid (particularly gas in the form of ventilated air) to pass from the air path to the interior of the sealing ring (401). This fluid communication port (452) may be located anywhere in the air path providing access to the inner volume (412) of the sealing ring (401). In the embodiment of FIG. 1 the port (452) is located near the distal end of the respiratory tube (205) providing fluid flow from the respiratory tube (205) to the inner volume (412) of the sealing ring (401). In the embodiment of FIG. 6, the port (452) comprises two holes located in the interior surface (677) of the sealing ring (401) providing fluid flow from the cavity (511) to the inner volume (412) of the sealing ring (401). In the embodiment of FIG. 8, the port (452) is an elongated generally continuous slit in the interior surface (677) which circumscribes the cavity (511). While these examples provide some embodiments, other fluid communication ports (452) may be used in other embodiments.

The respiratory tube (205) may be formed in any manner known to those of ordinary skill in the art but will generally form a smoothly curving hollow cylinder of generally circular or elliptical cross-section preferably approximating, for ease of insertion, the shape of the human throat. The respiratory tube (205) is preferably sized and shaped to accommodate the passage of endo-tracheal tubes and related medical devices up to 9 French in diameter. The length of respiratory tube (205) is such that when the laryngeal mask (100) is properly positioned for use within the oropharynx, the attachment (proximal) end (207) of respiratory tube (205) is located exterior to the oral cavity of the patient. The attachment end (207) of the respiratory tube (205) terminates in an unobstructed proximal lumen (209), providing a direct pathway through the respiratory tube (205) to the distal end (203) and distal lumen (523). In alternative embodiments, the attachment end (207) may be fitted with removable adapters or connectors (871) suitable for connection to a variety of medical devices, for example, lung ventilation machines.

Figure 10:
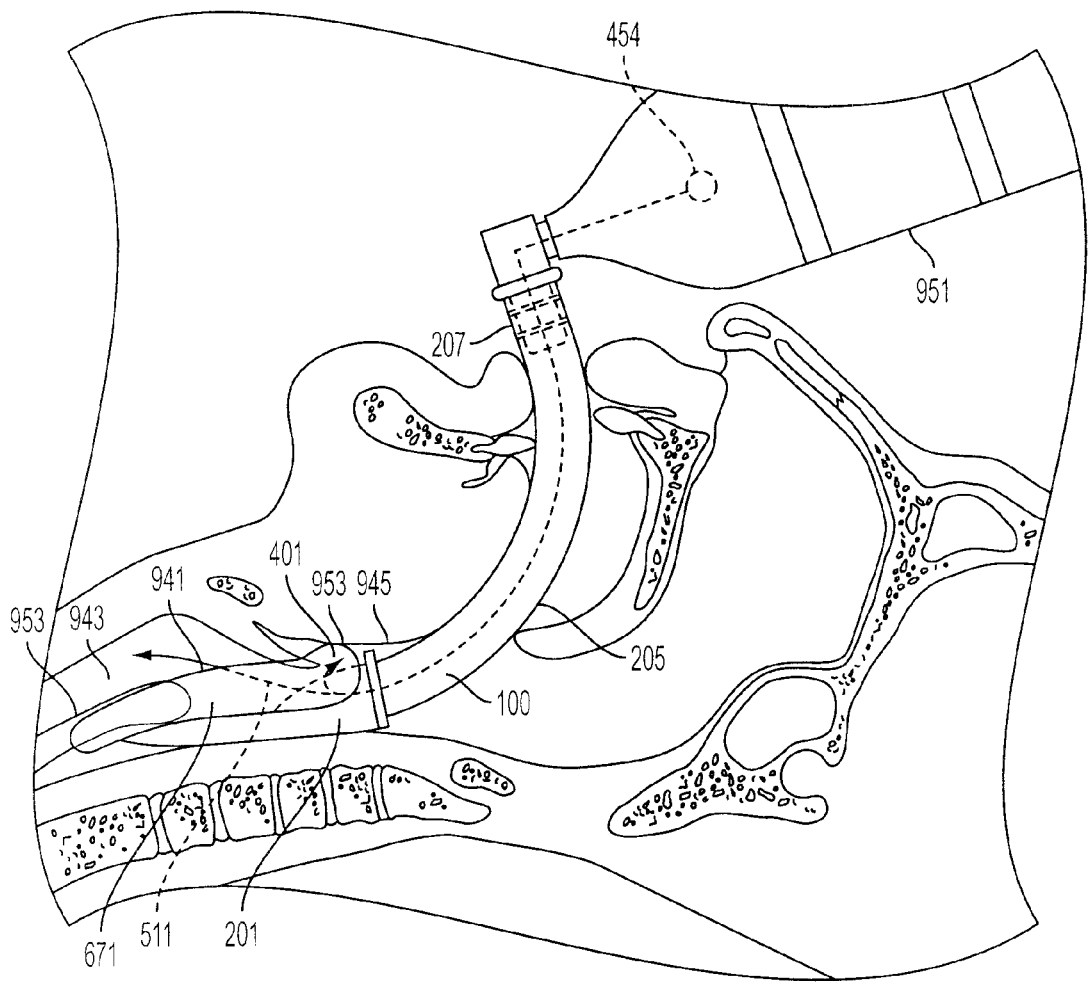
FIG. 10 shows an embodiment of a laryngeal mask in place in the throat of a patient.

As shown in FIG. 10, when the airway (100) is in place in a patient there is provided by the structure of the airway (100) an air flow passageway (454) for air to flow from external to the patient into the patient's lungs to provide for ventilation of the patient. This air flow generally comprises air passing into the attachment end (207) of the respiratory tube (205) from a ventilation apparatus, such as the squeeze bag (951) depicted in FIG. 9, or from a mechanical ventilator. That air then flows through the respiratory tube (205) and generally into the cavity (511) of the shield (201). As the shield (201) is over the laryngeal opening (941), which may be held open by the presence of the wedge (501), the air is then directed, at least in part, into the patient's lungs.

FIG. 10 shows how the sealing ring (401) and shield (201) are pushed against the surface of the throat (945) when air pressure inside the air path (454) from the attachment end (207) of the respiratory tube (205) to the patient's trachea (943) is increased. This occurrence is called "self-pressurizing" as the sealing ring (401) inflates, pressurizes, or otherwise adjusts using air being provided to the patient, instead of air separately provided to the sealing ring (401) through a separate inflation bulb or related device. Self-pressurization generally provides for increased sealing pressure of the shield (201) in the throat (945) during assisted inhalation. The pressure is due to expansion or other alteration of the sealing ring (401) as air in the respiratory pathway (454) (provided under a positive pressure to provide for positive-pressure ventilation of the patient) is able to pass through the communication port (452) and into the inner volume (412) of the sealing ring (401). Essentially, the expansion or alteration occurs as air forced into the lungs of the patient from an external source is also directed through the communication port (452) and into the inner volume (412) of the sealing ring (401). During positive-pressure ventilation, the ventilation apparatus will begin by forcing air from the squeeze bag (951) or similar device, through the connector (871) and into the respiratory tube (205). It will then flow into the cavity (511) via the distal end (203) of the respiratory tube (205). An increase in the air pressure inside the cavity (511) or tube (205) will also result in a simultaneous increase in air pressure within the sealing ring (401) and pushing of the structure of the sealing ring (401) into the structure of the throat (945) due to air passing through the communication port (452) and into the inner volume (412) of the sealing ring (401).

The sealing is best understood in conjunction with FIGS. 9 and 10. While the below discussion is believed to be a course of operation of the device, this is in no way intended to limit the invention to any particular theory of operation. When in place in the throat (945), the sealing ring (401) is generally in at least partial contact with the surface (953) of the throat (945) adjacent to or about the laryngeal opening (941). At this point the tissue pressure between the throat and airway (100) is generally reduced. This contact serves to define an air area comprising the cavity (511) which generally only has prepared access points being the laryngeal opening (941) and the respiratory tube (205). The seal between the sealing ring (401) and the surface (953) may or may not be complete, but is expected to be relatively complete in an embodiment of the inflation. As air is forced into the respiratory tube (205), the air pressure inside the respiratory tube (205) and the cavity (511) increases. This increase will push in all directions internal to the cavity (511) and will attempt to push the shield (201) away from the laryngeal opening (941). However, as the sealing ring (401) is flexible, air pressure on the upper surface (675) from air passing into the inner volume (412) will generally push the upper surface (675) toward the surface (953) of the throat (945) it is in partial contact with as illustrated by the arrows in FIG. 9. This will result in an increased connection pressure between the shield (201) and the throat (945). Further, as the pressure pushes the airway (100) away from the laryngeal opening (941) it will also generally push the posterior base (403) into the back of the throat further increasing the pressure.

The example of expansion shown in FIG. 9 illustrates an initial position of the sealing ring (401) in dashed line with the expanded position in solid line. The expansion occurs because the air pressure internal to the cavity will increase relative to the air pressure outside the shield during positive-pressure ventilation (201) as indicated by the arrows. As the sealing ring (401) is generally constructed of flexible material and fluid communication is allowed between the air path (454) and the inner volume (412) of the sealing ring (401), the material will move in response to the increased pressure increasing connection pressure to the throat (945). It should be apparent that while the air can flow into the inner volume (412) of the sealing ring (401) from a port (452) opening into the cavity (511), the port (452) can be positioned in other locations to allow such fluid communication. One such alternative is shown in FIG. 1 where the port (452) is between the respiratory tube (205) and the sealing ring (401).

As the seal pressure increases, so does the ability of the shield (201) to maintain the internal airflow from the ventilation apparatus directing additional air into the lungs of the patient. Once the lungs have been appropriately inflated, exhalation generally occurs by having the patient spontaneously breath out. Air escaping the patient's lungs will generally pass back from the lungs through the respiratory tube (205) and escape the patient. During exhalation, however, it is generally not necessary that the shield (201) be tightly sealed. If air was to escape the shield (201) by going around it, this air would still generally pass out of the mouth of the patient.

By allowing the shield (201) to self-pressurize when air pressure inside the airway (100) is increased by air being forced into the patient's lungs during assisted inhalation, and a decrease of the pressure during exhalation, the airway (100) significantly reduces the pressure placed on the throat (945) during the course of use of the airway (100). In particular, it is understood in the art that generally exhalation takes twice as long as inhalation, therefore the time that the throat is subject to the increased sealing pressure from the pressurized shield (201) is generally reduced by about two-thirds since the airway (100) is pressurized an increased amount only during inhalation. This can significantly reduce the potential for damage to pressure sensitive structures in the throat by simply reducing the amount of time, in any procedure, the structures are exposed to the increased pressure.

Further, the self-pressurization provides for some controlled monitoring of the pressure placed on the structures in the throat contacted by the shield (201). It is understood that when pressurizing the lungs of a patient during assisted inhalation, peak pressures should generally not be maintained above the range of about 60 cm of water as this can result in damage to the lungs. Pressures are generally maintained in the 15 to 30 cm of water range. For this reason, squeeze bags and other ventilation systems are generally inhibited from producing damaging pressure by their design and/or operation. It is also generally the understanding of the art that similar pressure ranges to those which are safe for lung inflation are also within a safe zone for inhibiting damage to throat structures. As the pressure inside the shield (201) is effectively limited to the maximum pressure provided by the attached ventilation apparatus, and since the ventilation apparatus is provided with a safe zone for lung ventilation which is believed inside the safe zone for throat damage, both body structures are simultaneously protected.

As should be apparent from the above discussion, the self-pressurization of the sealing ring (401) occurs by having the sealing ring (401) be in fluid communication with the air path (454) in such a fashion that when air is directed into the air path (454), there is an air pressure differential created inside the shield (201) which allows air to flow into inner volume (412) of the sealing ring (401) providing for pressurization of the flexible structures of the sealing ring (401) to expand and increase the contact pressure between the throat and the sealing ring (401).

In the embodiment of FIG. 1, communication is achieved by the presence of port (452) located in the respiratory tube (205) which directs air to an inner volume (412) of the sealing ring (401). This port (452) may be of any shape, size or arrangement but will generally be of sufficient size so as to allow free air communication between the air space inside the respiratory tube (205) and the space at least partially internal to the surface comprising the sealing ring (401). That is, air flow from the respiratory tube (205) can pass into the inner volume (412) of the sealing ring (401) without major interference from surface effects or the like. In the alternative embodiment of FIG. 6, the sealing ring (401) includes a port (452) which is a series of holes allowing fluid communication from the cavity (511) to the inner volume (412) of the sealing ring (401). The embodiment of FIG. 8 provides for a more continuous port (452) which is a slit around the inner side (677) of the sealing ring (401). These different embodiments still provide for the same net result. Air which is present inside the air path (454) is able to flow into the sealing ring (401).

One of ordinary skill in the art would see that the three depicted embodiments are not the only possible structures which would allow for fluid communication from the air path to the sealing ring (401). In an additional alternative embodiment, the port (452) could be replaced by alternative structures allowing fluid communication.

The airway (100), in an embodiment, may be constructed from a single blow-molded or injection molded construction which is formed into both the shield (201) and respiratory tube (205) by blowing or injecting suitable construction materials such as plastics or silicone into a shaped die. In such an embodiment, the entire airway (100) may be formed as a single piece. Often to facilitate such construction, the ventilation lumen (531) and distal lumen (533) would be sealed in the initial formation. The lumens (531) and (533) would then be punched or cut out from resultant structure to create the openings. The embodiment of FIG. 1 would generally be suitable for such single piece blow-molding construction. Alternatively, the airway (100) can be formed from a plurality of separately constructed pieces which are later connected together.

Blow-molding techniques generally require that the structure to be formed comprise a hollow balloon which is then pushed or molded into shape. FIG. 5 shows a cross-section of the shield of FIG. 3 indicating how the shield (201) is preferably constructed and how the balloon is compressed and formed into the desired structure shown in FIG. 3. As can be seen in FIG. 5, the sealing ring (401) and posterior base (403) are formed by taking the opposing sides of the balloon and partially pushing them together at an interior location so that they touch at a point spaced from the entry point (462) and the neck (508). These opposing sides are then adhered together either through the use of an adhesive or simply through the adhesive capabilities of the material being formed so as to form the posterior base (403) and sealing ring (401) as shown in the FIGS. As should be apparent, this style of formation results in a structure whereby the sealing ring (401) forms a generally toroidal structure including an inner volume (412) as discussed in conjunction with FIG. 1, and the posterior base (403) does not allow for air passage between the two surfaces which form its upper (402) and lower (404) portions thereby forming a generally solid base attached to the sealing ring (401) and resulting in the "dish" shape of FIG. 3.

As can be further seen in FIG. 5, the posterior base (403) is thicker than either of the outer surfaces (410) of the sealing ring (401) which provides additional strength to the shield (201) as a whole. At the same time, however, the structure is not rigid and is capable of bending during insertion. In a preferred embodiment, the outer surfaces (410) are in fact molded to be significantly thinner than each of the upper portion (402) and lower portion (404) to provide for even more strength to the posterior base (403) and to provide for improved mold flow characteristics.

Figure 2:
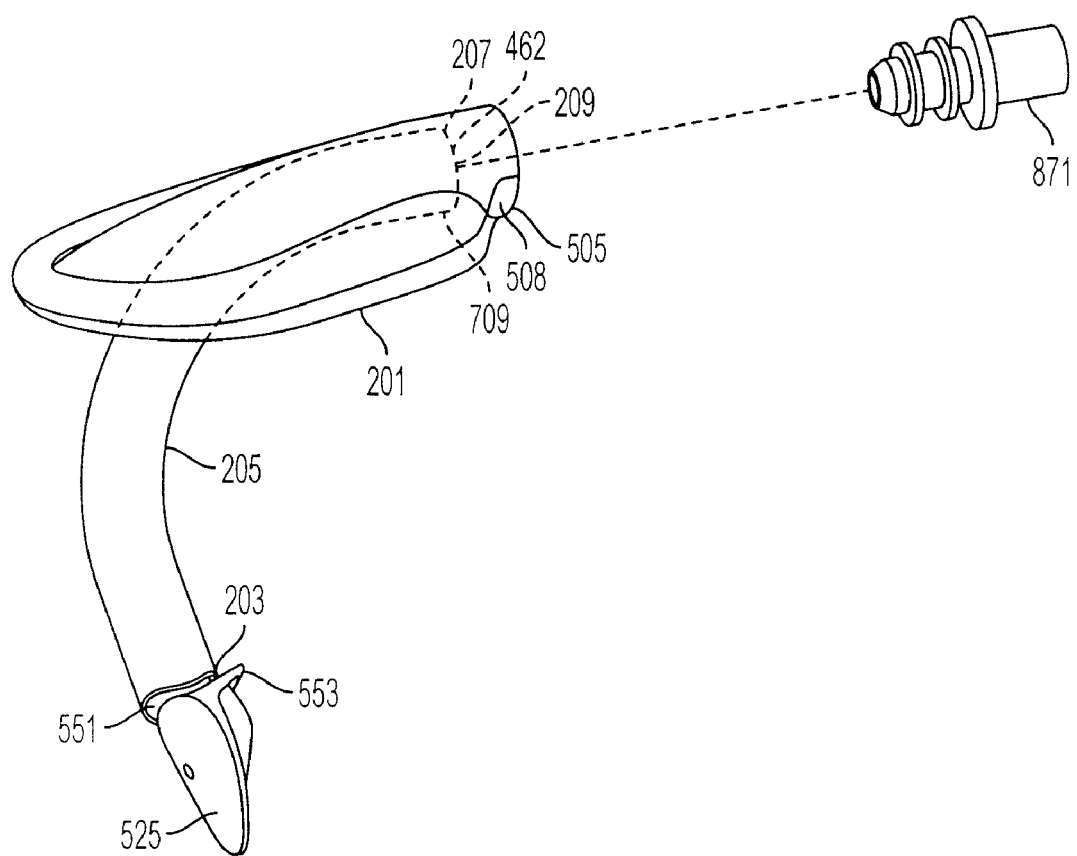
FIG. 2 shows a partially exploded view of the embodiment of FIG. 1 to show a manner of assembly.
Figure 3:
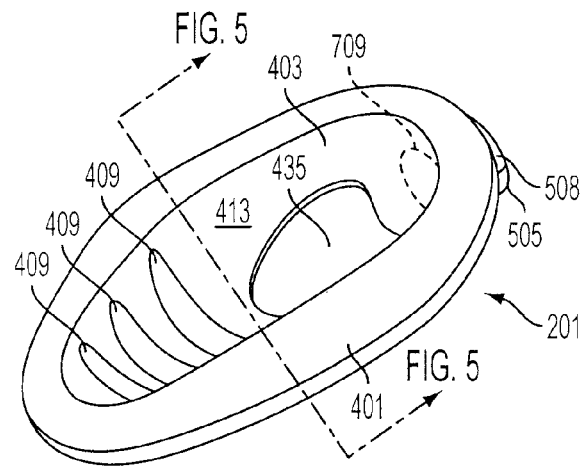
FIG. 3 shows a perspective view of a shield.
Figure 4:
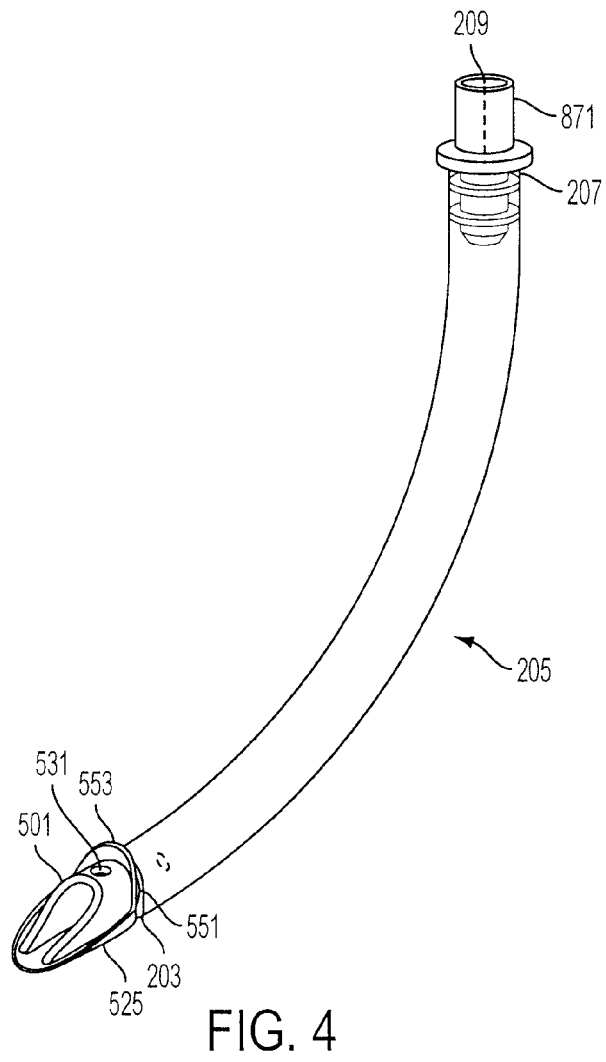
FIG. 4 shows a perspective view of a breathing tube.

In an embodiment where the airway (100) is comprised of two pieces, in order to assemble the embodiment of airway (100) shown in FIG. 1, it is generally preferred that the following steps be performed to assemble the components, generally as indicated in FIG. 2. First the components are formed as shown in FIGS. 3 and 4. The shield (201) has a hole (709) cut through the proximal wall of the cavity (511). As should be apparent from FIGS. 3 and 5, the entry point (462) and hole (709) therefore present a relatively straight passage which extends from inside the cavity (511) through the sealing ring (401) and out the proximal end (505). There is also generally formed a connection recess (435) in the posterior base (403). This may be cut out or may be formed by simple compression of the material forming the posterior base (403).

The respiratory tube (205) is now inserted, proximal end (207) first, through the hole (709), passed through the sealing ring (401), and extended out the entry point (462) and thus the posterior end (505) of the shield (201). The hole (709) and entry point (462) are preferably sized and shaped to be of relatively similar size to the exterior diameter of the respiratory tube (205) so that a tight connection is formed by the respiratory tube (205) distending the material of the shield (201) slightly in both places. The respiratory tube (205) will continue to be slid through the hole (709) and entry point (462) until the hole (709) interacts with the groove (551) and disk (553). At that point, the wedge (501) and disk (553) will generally be the only portions of the respiratory tube (205) which has not passed through the hole (709), the reinforced support (525) will be adjacent to the recess (435) in the posterior base (403), and the fluid communication port (452) is internal to the sealing ring (401) allowing air in the respiratory tube (205) to flow into the sealing ring (401). These pieces will then be connected together resulting in the wedge (501) being positioned in the cavity (511) and generally flush with the interior of the posterior base (403). The connection between the posterior base (403) and the reinforced support (525) may be formed in any manner known to one of ordinary skill in the art, however, in a preferred embodiment, the two devices are adhered together with a generally non-separable adhesive. The respiratory tube (205) now is arranged to generally pass through the sealing ring (401) allowing air flow from the respiratory tube (205) into both the interior of the sealing ring (401) and the cavity (511).

In the depicted embodiment, the disk (553) and groove (551) formed toward the distal end (203) of the respiratory tube (205) serve to reinforce the connection (703). In particular, the material surrounding the hole (709) will end up being stretched by the passing of the respiratory tube (205) until the hole (709) is aligned with the groove (551). The material will then relax and the hole (709) will collapse slightly into the groove (551). This provides a first level of support. The disk (553) adjacent to the hole (709) can then be provided with an adhesive which adheres to the shield (201).

While in the above embodiment, as depicted in FIG. 2, the proximal end (207) of the respiratory tube is first threaded through the hole (703) and entry point (462), in an alternative embodiment, the wedge (501) and respiratory tube (403) may actually be inserted in the opposing direction to the embodiment shown in FIG. 2. In this alternative embodiment, the wedge section and the distal end (203) of the respiratory tube (205) would be first inserted through the entry point (462), run through the sealing ring (401), and exit the hole (703). While this method is viable in most cases, it is generally not preferred as it is usually more difficult to perform. Further, in some embodiments, it may require redesign of the wedge section components (such as the wedge (501), disk (553), or reinforced support (525)), to prevent damage to the hole (703) and entry point (462) during the wedge (501) passing through those structures.

Generally, use of the airway (100) would proceed as follows. Before insertion, the sealing ring (401) would be in a neutral position, generally at an ambient internal pressure, and there would be little or no positive pressure created within the air path (454). The mouth of the patient is opened and their head positioned for insertion of the airway (100). The shield (201) is pushed into the orolaryngeal region. The smooth arcuate curves of the combined respiratory tube (205) and shield (201) positions the laryngeal mask (100) in alignment with the laryngeal opening (741). Upon proper positioning, as generally determined by a resistance to further forward motion, the airway (100) is considered placed. A breathing device or machine, such as a ventilator or a squeeze bag (951) would then be coupled to the attachment end (207) of the respiratory tube (205).

Positioned within the cavity (511), the distal lumen (523) is axially aligned with the laryngeal opening (941), permitting positive-pressure lung ventilation to be performed through the airway (100), or allowing endo-tracheal tubes or related medical instruments inserted through the respiratory tube (205) to exit through the distal lumen (523) which is directly aligned for passage into the laryngeal opening (941). Removal of the airway (100) is normally the reverse of the insertion procedure described above. As the device is generally relatively inexpensive to manufacture, once it has been removed the airway (100) will generally be discarded. However, in an alternative embodiment it may be sterilized and reused in any manner understood by those of ordinary skill in the art.

During assisted positive-pressure ventilation, the airway (100) would operate as follows. When a breath is provided for the patient, the ventilator or other device would be used to increase air pressure inside the respiratory tube (205) forcing air into the tube (205) and toward the cavity (511). As the air pressure increases along the tube (205) and/or cavity (511), some of the air being pressed toward the patient will enter the port (452) and flow into the sealing ring (401), while other air will continue to flow out the wedge (501) and into the cavity (511) and the trachea (943) and lungs of the patient. The pressure of air flowing into the lungs, and the pressure of air flowing into the sealing ring (401) will generally be relatively equal. As there is generally no external escape for the air in the air path, the sealing ring (401) will generally pressurize causing it to seal tighter within the throat (945). This will force the airway (100) into stronger contact with the walls of the throat (945) and surface (951). As the shield (201) and throat (945) are pressed together, they will form a stronger seal and will inhibit air from inside the cavity (511) from passing between them, instead directing that air into the lungs of the patient. This process will continue as long as air is under positive pressure and directed toward the lungs by the ventilation apparatus.

Once the inhalation is complete, the pressure will generally be decreased inside the air path (454). This will result in the pressure in the air path (454) decreasing back toward ambient and the sealing ring (401) decreasing the pressure imparted by the airway (100) to the throat (945). As the patient begins to exhale (generally by spontaneous exhalation), the patient will push air back toward the airway (100). This air will generally pass into the cavity (511) and then flow out into the respiratory tube (205) and escape the patient's body. Some of such air may pass into the sealing ring (401) and serve to increase the pressure slightly, but this will generally result in a pressure between the sealing ring (401) and the throat (945) still being significantly less than that during the assisted inhalation Alternatively, some air may escape around the edges of the shield (201). As the pressure of spontaneous exhalation is generally insufficient to result in opening of the esophageal sphincter, this air will generally escape around the airway (100) and exit the patient through their mouth or nose. Once exhalation is complete, the process will generally repeat beginning with another inhalation.

The elimination of the need to tightly seal the shield (201) during exhalation with as much pressure as during inhalation relates in part to the expected behavior of air during inhalation and exhalation. It is undesirable for air, during forced inhalation to be able to proceed down the esophagus. At sufficient pressure to inflate the lungs there is also generally sufficient pressure to open the esophageal sphincter and allow air to enter into the stomach. Forcing air into the stomach can create a potentially dangerous situation. Therefore, during this forced inhalation, it is desirable that the shield (201) seal strongly so as to provide an air passage into the laryngeal opening (941) without allowing the pressurized input air to escape into the stomach. The airway (100) carries out this task since the tightness and inflation of the sealing ring (401) to the throat (945) increases proportionate to the force of air within the passageway. As the air pressure increases in the passageway (approaching levels where air could be forced in the stomach), the sealing ring (401) inflates and improves the tightness of its seal to the throat (945), inhibiting air from passing outside of the air passage and directing that air into the lungs.

During spontaneous exhalation, the pressure produced by the patient's lungs is generally insufficient to force air past the esophageal sphincter, and thus there is a decreased need for the airway (100) to be tightly sealed to the laryngeal opening (941). While it is expected that most air will in fact flow out the respiratory tube (205) as the path of least resistance, even if it does not, the air which escapes will have insufficient force to push past the esophageal sphincter and will instead escape around the airway (100) and out the mouth or nose as in normal breathing.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

The invention claimed is:

1. A supraglottic airway comprising;
   a respiratory tube having a distal end, a proximal end, and a length therebetween, said respiratory tube having a hollow interior and a port within said length between said distal end and said proximal end; and
   a shield comprising a posterior base and a sealing ring surrounding said posterior base and defining an inner volume within said sealing ring and a cavity above said posterior base;
   wherein said shield is attached to said distal end of said respiratory tube so that said hollow interior of said respiratory tube is in fluid communication with said cavity via said distal end; and
   wherein said inner volume of said sealing ring is capable of fluid communication with said hollow interior via said port.

2. The airway of claim 1 wherein said respiratory tube is smoothly curved.

3. The airway of claim 1 wherein said shield is formed by blow-molding.

4. The airway of claim 1 wherein said shield formed by injection molding.

5. The airway of claim 1 wherein said port comprises a single hole.

6. The airway of claim 1 further comprising a connector removeably attached to said proximal end of said respiratory tube.

7. The airway of claim 1 wherein the airway is intended to be disposed of after a single use.

8. The airway of claim 1 wherein the airway is intended for reuse.

9. A supraglottic airway comprising;
   a respiratory tube having a distal end, a proximal end, and a length therebetween, said respiratory tube defining an air path therethrough and having a port within said length between said distal end and said proximal end; and
   a shield comprising a posterior base and a sealing ring surrounding said posterior base and defining an inner volume within said sealing ring and a cavity above said posterior base, wherein said shield is attached to said distal end of said respiratory tube so that said air path in said respiratory tube is in fluid communication with said cavity via said distal end, and wherein said inner volume is in fluid communication with said air path via said port.

10. A supraglottic airway comprising;
    a respiratory tube having a distal end, a proximal end, and a length therebetween, said respiratory tube defining an air path therethrough and having a port within said length between said distal end and said proximal end; and
    a shield comprising a posterior base and a sealing ring surrounding said posterior base and defining an inner volume within said sealing ring, wherein said shield is attached to said distal end of said respiratory tube so that said air path in said respiratory tube is in fluid communication with said cavity via said distal end and said inner volume of said sealing ring via said port.

11. A method of providing an artificial airway to a human comprising:
    placing in the throat of a human, a supraglottic airway comprising;
       a respiratory tube having a distal end, a proximal end, and a length therebetween, said respiratory tube defining a hollow interior and having a port within said length between said distal end and said proximal end; and
       a shield comprising a posterior base and a sealing ring surrounding said posterior base and defining an inner volume within said sealing ring and a cavity above said posterior base, wherein said shield is attached to said distal end of said respiratory tube said cavity and said hollow interior jointly defining an air path;
    attaching said proximal end to a ventilation apparatus; and
    forcing air into said air path to provide air to said patient said air passing from said hollow interior, through said distal end, and into said cavity;
    wherein, the act of forcing air into said air path alters the pressure in said inner volume of said sealing ring due to air passing from said hollow interior, through said port, and into said inner volume.

12. The method of claim 11 wherein said alteration of pressure in said inner volume of said sealing ring comprises altering the size of said sealing ring as air is forced into said air path.

13. The method of claim 11 wherein said alteration of pressure in said inner volume of said sealing ring increases the strength of seal of said sealing ring to said throat.

14. The method of claim 11 wherein said alteration of pressure in said inner volume of said sealing ring increases the pressure said sealing ring imparts on said throat.

15. An artificial breathing system comprising:
    a supraglottic airway including;
    a respiratory tube having a distal end, a proximal end, and a length therebetween, said respiratory tube defining a hollow interior therethrough and having a port within said length between said distal end and said proximal end; and
    a shield comprising a posterior base and a sealing ring surrounding said posterior base and defining an inner volume within said sealing ring and a cavity above said posterior base, wherein said shield is attached to said distal end of said respiratory tube and said cavity and said hollow interior jointly define an air path; and
    a ventilation apparatus designed to increase pressure in said air path which is attached to said proximal end;
    wherein, when said ventilation apparatus increases pressure in said air path it also alters the pressure in said inner volume in said sealing ring via air flow from said hollow interior through said port.

16. The system of claim 15 wherein said alteration of pressure in said inner volume in said sealing ring comprises altering the size of said sealing ring as air is forced into said air path.

17. The system of claim 15 wherein said alteration of pressure in said inner volume in said sealing ring increases the strength of seal of said sealing ring to said throat.

18. The system of claim 15 wherein said alteration of size of said sealing ring increases the pressure said sealing ring imparts on said throat.

19. The system of claim 15 wherein said port comprises a single hole.

20. A supraglottic airway comprising;
- a respiratory tube having a distal end, a proximal end, and a length therebetween, said respiratory tube having a hollow interior;
- a shield comprising a posterior base and a sealing ring surrounding said posterior base and defining a cavity above said posterior base; and
- means for allowing fluid communication between an inner volume of said sealing ring and said hollow interior of said respiratory tube, said means being within said length and between said distal end and said proximal end; and
- separate means for allowing fluid communication between said hollow interior and said cavity.

* * * * *